United States Patent [19]

Treacy et al.

[11] Patent Number: 5,142,074

[45] Date of Patent: Aug. 25, 1992

[54] HIGH PURITY COPPER ALKOXIDES

[75] Inventors: Debra J. Treacy, Walpole, Mass.; Khodabakhsh S. Mazdiyasni, La Mesa, Calif.

[73] Assignee: General Atomics, San Diego, Calif.

[21] Appl. No.: 688,375

[22] Filed: Apr. 19, 1991

Related U.S. Application Data

[60] Continuation of Ser. No. 537,923, Jun. 13, 1990, abandoned, which is a division of Ser. No. 306,539, Feb. 3, 1989, Pat. No. 5,006,508.

[51] Int. Cl.$^5$ .......................... C07F 1/08; C01G 3/02; H01L 39/12
[52] U.S. Cl. .................... 556/113; 505/735; 505/810; 505/811; 505/1
[58] Field of Search ................ 556/113; 505/735, 810, 505/811

[56] References Cited

U.S. PATENT DOCUMENTS

| | | | |
|---|---|---|---|
| 3,403,163 | 9/1968 | Fuchsman | 556/113 |
| 3,538,168 | 11/1970 | Mitchell | 556/113 |
| 4,847,239 | 7/1989 | Piotrowski et al. | 505/801 |

OTHER PUBLICATIONS

Singh, J. V.; Baranwal, B. P.; and Mehrotha, R. C., "Synthesis and Characterization of Some Alkoxide Derivatives of Copper (II)", Z. anorg. allg. chem., vol. 477, pp. 235–240 (1981).

Cotton, F. A., and Wilkinson, G., *Advanced Inorganic Chemistry A Comprehensive Text*, N. Y., Wiley–Interscience, 4th Edition, p. 256, 1980.

Nebergall, Holtzclaw, and Robinson, "College Chemistry with Qualitative Analysis", D.C. Health and Co., Lexington, Mass., 6th Ed., p. 884, 1980.

*Primary Examiner*—José G. Dees
*Assistant Examiner*—Porfirio Nazario
*Attorney, Agent, or Firm*—Fitch, Even, Tabin & Flannery

[57] ABSTRACT

The invention relates to the preparation of high purity, chloride- and alkali metal-free copper (II) alkoxides by means of the reaction of an alcoholic alkali metal alkoxide solution with copper (II) fluoride; ammoniating the resulting solution to render soluble the resulting copper (II) alkoxide; and filtering the resulting solution to obtain an alkali metal- and chloride-free alcoholic copper (II) alkoxide solution. The resulting solution is useful in the preparation of superconducting compound such as yttrium-barium-copper oxide superconductor.

5 Claims, No Drawings

HIGH PURITY COPPER ALKOXIDES

This application is a continuation of application Ser. No. 537,923 filed Jun. 13, 1990, now abandoned, which is a division of Ser. No. 306,539, filed Feb. 3, 1989, now U.S. Pat. No. 5,006,508.

This invention relates to the preparation of ultra-pure copper alkoxides. In particular, this invention relates to a process for the preparation of impurity-free, especially chloride-free, ultra-pure copper alkoxides suitable for use in the preparation of superconductive ceramic materials.

BACKGROUND OF THE INVENTION

In the field of superconductive ceramic materials, large advances have been made since the 1970's, and in particular, since 1985. Whereas a decade or so ago superconductivity was observed only at or near the liquid helium temperature, of 1° Kelvin (K), recent advances have raised the superconducting temperature to nearly 100° K. These advances have now brought superconducting ceramics within the temperature range of liquid nitrogen which results in considerable cost savings. While many factors have contributed to expanding the temperature range of superconductive materials, one of the important requirements is the use of materials in the manufacture of superconducting ceramics which will not leave undesirable impurities in the final product. Among the more ubiquitous impurities which might find their way into finished superconducting ceramics are carbon, aluminum, silicon and chlorine (as chloride ion).

The earliest of the higher temperature superconducting ceramic materials were quaternary ceramics composed of yttrium or a lanthanide series rare earth metal, an alkaline earth metal such as barium or strontium, copper and oxygen. More recent discoveries have brought forth five component superconducting ceramics such as the thallium-calcium-barium-copper-oxygen series of materials. While the mechanism by which these ceramic materials are superconducting is not fully understood, there is some speculation that the electrons flowing in these superconducting ceramics travel through "tunnels" formed by alternating layers of metal and oxide ions. While the crystal structure of these ceramics is complex and not fully determined, it is known that they are layered structures sensitive to moisture, heat and pressure. It is further known that distortions in the crystal structure can greatly decrease or completely destroy the superconducting properties of the ceramic material. These distortions can be created in the crystal by the inclusion of larger or smaller ions within the crystal lattice. It is easier to envision such a distortion using a larger ion.

Imagine a large box full of baseballs neatly stacked in layers, one on top of the other and held in place by the walls of the box. The void space between the baseballs would be the "tunnels" through which "electrons" would flow. However, if a basketball were placed in the center of the box, the layered order of the baseballs would be locally destroyed and the flow of "electrons" blocked. Likewise, small marbles placed in void spaces formed by the baseball layers would block the flow of "electrons." For these reasons, impurities such as carbon, aluminum, silicon and chloride ion are not desirable in a superconducting ceramic.

The reported superconducting ceramics have been prepared by thermal conversion using various inorganic salts such as nitrate, carbonate or metal-organics such as alkoxide starting materials. Care in preparation of these starting materials will eliminate silicon and other cations as impurities. Thermal conversion at 800°–1000° C. in an oxygen rich atmosphere causes the carbon present in the starting materials to be oxidized to carbon dioxide gas which volatilizes from the ceramic product, thereby removing carbon as an impurity. Nitrate decomposes to volatile nitrogen oxides and likewise escapes from the ceramics. While nitrates do not leave impurities in the ceramic product, their use creates air pollution control problems in a production scale-up. The removal of chloride, however, cannot so readily be accomplished.

While chloride may not, at first glance, seem to be a problem in the production of superconducting materials, in actual fact chloride salts are frequently used as the base materials from which the carbonates, nitrates and alkoxides are prepared. During these preparations, trace amounts of chloride ion trail along with the carbonate, nitrate or alkoxide product. Removal of the trace chloride may entail numerous purification steps and be prohibitively expensive. Among the most difficult of the raw materials to purify are the copper (II) alkoxides used in the preparation of superconducting ceramics. The terms copper (II) and cupric refer to copper in the +2 valence state.

The most common method of preparing a copper (II) alkoxide has been the reaction of an alcoholic solution of anhydrous cupric chloride with an alcoholic solution of an alkali metal alkoxide prepared in situ by reacting an alkali metal with an excess of an alcohol. While any of the alkali metals may be used, the preferred metal is lithium for safety reasons. The alcohol is typically one of $C_1$ to $C_4$ alcohols, although others may be used when desirable. A typical reaction may be that between lithium metal and anhydrous methanol to produce a methanolic solution of lithium methoxide. This lithium methoxide solution is filtered to remove any precipitate that may have formed, and the filtered solution is added to a solution of anhydrous cupric chloride in anhydrous methanol. The lithium methoxide and cupric chloride react to form copper (II) methoxide, which precipitates, and lithium chloride which is soluble in methanol. The copper methoxide is collected by filtration and washed with several methanol washes.

While the reaction of cupric chloride and lithium methoxide seemingly separates the copper (II) methoxide from lithium chloride; in fact, some of lithium chloride and also cupric chloride may become entrained in the precipitate. While washing the precipitated copper (II) methoxide with methanol may remove some of the chloride compounds, sufficient chloride may remain to adversely affect superconductivity in the final ceramic product. It would be preferable that the copper (II) methoxide remain in solution and that the chloride-containing compounds precipitate. Being aware of the difficulties encountered in the preparation of copper (II) alkoxides, this invention presents a new method for the preparation of copper (II) alkoxides uncontaminated by chloride-containing materials. Specifically, the invention relates to the preparation of ultra pure copper (II) alkoxides wherein the copper (II) alkoxide is free of anions as well as any cations which may adversely affect the superconducting properties of copper containing superconducting ceramics.

DETAILED DESCRIPTION OF THE INVENTION

This invention relates to the preparation of high purity copper (II) alkoxides, said copper (II) alkoxides being essentially free of contaminating anions or cations which could adversely affect the superconducting properties of copper-containing superconducting ceramics. As used in this description, the terms solution and solution mixture mean a homogeneous solution, or a solution which contains a precipitate or suspension of some materials. Where necessary the text will clearly state which is meant. Solutions obtained after filtration and prior to any subsequent reaction or treatment do not contain a precipitate.

The method of this invention for the preparation of high purity copper (II) alkoxides comprises the steps of (a) reacting an alkali metal with an anhydrous, deoxygenated $C_1$ to $C_8$ alcohol and filtering the resulting reaction product to obtain an anhydrous, deoxygenated alcoholic alkali metal alkoxide solution, Solution A; (b) adding anhydrous copper (II) fluoride to Solution A to form an alcoholic copper (II) fluoride-alkali metal alkoxide solution mixture, Solution B; (c) heating Solution B to a temperature in the range of about ambient temperature to about 10° C. below the boiling point of the alcohol being used for a length of time in the range of about 0.25 hour to about 8 hours to form a solution mixture containing an alkali metal fluoride and a copper (II) alkoxide solution, Solution C; (d) ammoniating Solution C with anhydrous ammonia to form a saturated ammoniacal alcoholic solution mixture containing ammoniacal copper (II) alkoxide in solution and an alkali metal fluoride and cupric fluoride precipitate, Solution D; and (e) filtering Solution D to remove the alkali metal fluoride and cupric fluoride precipitate and obtain an alkali metal-free copper (II) alkoxide solution useful in the manufacture of superconductive compounds, Solution E. A dry, powdered, anhydrous copper (II) alkoxide that is useful in the manufacture of superconductive compounds can be obtained from Solution E by evaporation of the ammonia and the excess alcohol.

The ammoniacal, alkali metal-free copper (II) alkoxide solution, Solution E, prepared above may be used to prepare a homogeneous sol/gel that can be used to prepare superconducting ceramics. In the preparation of such a sol/gel, the ammoniacal copper (II) alkoxide solution, Solution E, is first hydrated by the addition of 2 moles of water for each mole of copper (II) alkoxide present. The solution is stirred from between 0.5 hour to about 2 hours to assure that the copper (II) ions are completely hydrated. The solution pH, during the hydration step, measures above 11. After the hydration has been completed, a hot solution of barium alkoxide in excess alcohol is added to the hydrated copper (II) solution. It is desirable that the barium alkoxide solution be at a temperature greater than 50° C. Thus, although methanolic or ethanolic solutions of a barium alkoxide could be used, it is desirable to use one of the higher boiling alcohols such as propanol, isopropanol, butanol, 2-butanol and the like. The amount of barium alkoxide added to the hydrated copper (II) solution is such that the barium-copper ratio is about 2:3. After the addition of the barium alkoxide to the hydrated copper (II) solution, the resulting solution mixture is heated at a temperature in the range of about 60° C. to about 70° C. for a time period in the range of about 0.5 hour to about 2.0 hours. The resulting barium-copper solution is a green color and is somewhat viscous. After the mixing of the barium-copper solution is completed, an alcoholic lanthanide series metal alkoxide solution, such as a yttrium alkoxide solution, a gadolinium alkoxide solution, a lanthanum alkoxide solution and the like, is added to the barium-copper mixture. The amount of the lanthanide metal alkoxide added is such that the lanthanide metal-barium-copper ratio is about 1:2:3. After the addition of the lanthanide metal alkoxide is completed, the resulting solution mixture is and heated to a temperature in range of about 50° C. to about 60° C. for a time period in the range of about 8 hours to about 16 hours. The resulting solution is a viscous sol. Upon concentrating and aging the sol, it turns into a sol/gel which can be used to prepare superconducting ceramics by methods known in the art. In choosing the alkoxide/alcohol used with the lanthanide metal, the same considerations should be taken into account as with the choice of the barium alkoxide. While any of the $C_3$ or higher alcohols may be used to prepare the alcoholic barium and lanthanide metal alkoxides, for economic reasons, isopropanol is preferred.

The copper (II) alkoxides prepared according to this invention utilize the fact that both copper (II) fluoride and lithium fluoride are insoluble in alcohols. (*Handbook of Physics and Chemistry*, 48th Ed., Chemical Rubber Co., 1968). While copper (II) fluoride may be insoluble in an alcohol, it is found, nonetheless, to be reactive toward reagents such as alkali metal alkoxides. Reaction between copper (II) fluoride and lithium alkoxide in alcohol solution produces an insoluble lithium fluoride and an insoluble copper (II) alkoxide. However, upon the addition of ammonia, the copper (II) alkoxide forms an ammoniacal copper (II) alkoxide complex which is soluble in the alcohol whereas lithium fluoride and copper fluoride do not form such soluble complexes and remain insoluble. Therefore, by ammoniating the reaction mixture and filtering the resulting ammoniacal solution, an ammoniacal copper (II) alkoxide solution, free of anions or cations which may adversely affect superconductivity, can be obtained. The resulting filtered solution may be used as is for the preparation of superconducting ceramics by methods such as the sol-gel method, or the alcohol and ammonia may be removed in vacuo, by heating or by a combination thereof to produce a dry, solid copper (II) alkoxide product which can be used in the preparation of superconducting ceramics.

The alkali metals used in the present invention may be selected from the group consisting of lithium, sodium or potassium, although lithium is preferred because it is the safest to use. The alcohol used to prepare the copper (II) alkoxide of the present invention may be selected from the group consisting of linear, branched or cyclic aliphatic $C_1$ to $C_8$ alcohols such as methanol, ethanol, propanol, isopropanol, butanol, octanol, cyclohexanol and the like. The preferred alcohol is methanol.

The examples which follow are for illustration purposes and are not meant to be limiting. Standard dry box and inert atmosphere techniques were used throughout the preparation of the copper (II) alkoxides of this invention.

EXAMPLE I

A 0.625 g sample of clean lithium metal was reacted with 300 ml of deoxygenated, anhydrous methanol under an inert atmosphere and filtered to remove any precipitated material. A 4.57 g sample of pure white anhydrous copper (II) fluoride was added to the filtered lithium methoxide solution and the resulting solution mixture was heated to 45°–50° C. for 0.5 hour to facilitate the formation of copper (II) methoxide which formed as a blue-grey precipitate. After cooling and allowing the reaction solution mixture to stand at ambient temperature for about 2.0 hours, the solution mixture was ammoniated by passing anhydrous ammonia through the solution. The solution turned a very dark blue upon the addition of ammonia, thereby indicating the complexing of copper (II) methoxide by ammonia. The resulting ammoniacal solution was filtered to give a clear, dark blue solution and a precipitate of lithium fluoride and unreacted copper (II) fluoride. The resulting clear, dark blue, ammoniacal copper (II) methoxide solution was used as is for the preparation of a yttrium-barium-copper-oxygen superconducting ceramic according to known art.

EXAMPLE II

The same procedure as Example I was followed to obtain a clear, dark blue, ammoniacal copper (II) methoxide solution after filtration and removal of lithium fluoride and copper (II) fluoride. This solution was evaporated to dryness in vacuo. As the ammonia and methanol were removed from the solution, copper (II) methoxide precipitated as a blue-grey powder. A sample of the powder was hydrolyzed and tested for the presence of lithium by the lithium flame test. No lithium was detected. The remaining powder was calcined and used to manufacture a yttrium-barium-copper-oxygen superconducting ceramic according to known art.

EXAMPLE III

A nomogeneous sol/gel, useful for the preparation of superconducting ceramics, was prepared in the following manner:

(a) Two moles of the triply-distilled water were added in a dropwise manner to 1 mole of a 0.21 Molar ammoniacal copper (II) methoxide solution prepared according to Example I. The pH of the resulting hydrated ammoniacal copper (II) methoxide solution was greater than 11. The resulting clear blue solution was stirred at ambient temperature for about 1 hour to ensure complete hydration of the copper (II) methoxide.

(b) A hot solution of barium isopropoxide, temperature greater than 53° C., was then added to the hydrated ammoniacal copper (II) methoxide prepared in (a). The barium-copper ratio of the resulting solution was about 2:3. The resulting barium-cop solution was mixed for about 1 hour at a temperature in the range of 600° C. to about 70° C. to yield a green, moderately viscous barium-copper solution.

(c) To the barium-copper solution resulting from (b), a solution of yttrium isoproxide in excess isopropanol was added in a dropwise manner. The resulting yttrium-barium-copper solution, which had a yttrium-barium-copper ratio of about 1:2:3, was stirred for a time in the range of 1 hour to about 4 hours at a temperature in the range of from about 50° C. to about 600° C. The resulting yttrium-barium-copper solution was a viscous sol which was concentrated and aged under conditions known in the art.

The sol/gel of (c) was used to prepare a yttrium-barium-copper-oxygen superconducting ceramic by thermal conversion methods known in the art.

EXAMPLE IV

A homogeneous sol/gel, useful for the preparation of superconducting ceramic, was prepared according to Example III, the difference being that yttrium isopropoxide was replaced with lanthanum isoproxide. The sol/gel so prepared was used to prepare a lanthanum-barium-copper-oxygen superconducting ceramic by thermal conversion methods known in the art.

What is claimed is:

1. A method for the manufacture of high purity copper alkoxides comprising the steps of:
   (a) reacting an alkali metal with an anhydrous, deoxygenated alcohol and filtering the resulting reaction product to obtain an anhydrous, deoxygenated alcoholic alkali metal alkoxide solution;
   (b) Adding anhydrous copper (II) fluoride to the solution to form an alcoholic copper (II) fluoride-alkali metal alkoxide solution;
   (c) heating the solution to a temperature in the range of from about ambient temperature to about 10° C. below the boiling point of the alcohol being used for a length of time in the range of about 0.25 hour to about 8 hours to form a solution containing an alkali metal fluoride and a copper (II) alkoxide;
   (d) ammoniating the solution with anhydrous ammonia to form a saturated ammoniacal alcoholic solution containing ammoniacal copper (II) alkoxide in solution and an alkali metal fluoride precipitate;
   (e) filtering the solution to remove the alkali metal fluoride precipitate and obtain an alkali metal-free ammoniacal copper (II) alkoxide solution; and
   (f) evaporating the ammonia and the excess alcohol from the solution to obtain a dry, powdered, anhydrous copper (II) alkoxide useful in the manufacture of superconductive compounds.

2. A method in accordance with claim 1 wherein the anhydrous alcohol is a linear, branched or cyclic $C_1$ to $C_8$ anhydrous aliphatic alcohol.

3. A method in accordance with claim 1 wherein the anhydrous alcohol is anhydrous methanol.

4. A method in accordance with claim 1 wherein the alkali metal is selected from the group consisting of lithium, sodium and potassium.

5. A method in accordance with claim 1 wherein the alkali metal is lithium.

* * * * *

UNITED STATES PATENT AND TRADEMARK OFFICE
CERTIFICATE OF CORRECTION

PATENT NO.   : 5,142,074
DATED        : August 25, 1992
INVENTOR(S)  : General Atomics It is certified that error appears in the above-identified patent and that said Letters Patent is hereby corrected as shown below:

| Col. | Line | Errors |
|---|---|---|
| Title page: Item (75) : | Inventor | After "Mazdiyasni" change "La Mesa" to --Alpine-- |
| 4 | 11 | After "is" insert --mixed-- |
| 4 | 11 | After "in" insert --the-- |
| 5 | 36 | Change "nomogeneous" to --homogeneous-- |
| 5 | 51 | Change "barium-cop" to --barium-copper-- |
| 5 | 52 | Change "600° C." to --60° C.-- |
| 6 | 4 | Change "600° C." to --60° C.-- |

Signed and Sealed this

Nineteenth Day of October, 1993

Attest:

BRUCE LEHMAN

Attesting Officer

Commissioner of Patents and Trademarks